(12) United States Patent
Vaz et al.

(10) Patent No.: US 10,100,461 B2
(45) Date of Patent: Oct. 16, 2018

(54) MONOFILAMENT OR MULTIFILAMENT HPPE YARNS

(75) Inventors: Claudia Maria Vaz, Maastricht (NL); Gerardus Aben, Monfort (NL); Edith Elisabeth Van Den Bosch, Riemst (BE); Christiaan Henri Peter Dirks, Dilsen (BE); Paulus Johannes Hyacinthus Marie Smeets, Geulle (NL)

(73) Assignee: DSM IP ASSETS B.V., Heerlen (NL)

( * ) Notice: Subject to any disclaimer, the term of this patent is extended or adjusted under 35 U.S.C. 154(b) by 1000 days.

(21) Appl. No.: 13/502,910

(22) PCT Filed: Nov. 12, 2010

(86) PCT No.: PCT/EP2010/067334
§ 371 (c)(1),
(2), (4) Date: Dec. 3, 2012

(87) PCT Pub. No.: WO2011/058123
PCT Pub. Date: May 19, 2011

(65) Prior Publication Data
US 2014/0147671 A1    May 29, 2014

(30) Foreign Application Priority Data

Nov. 13, 2009  (EP) .................................... 09175932

(51) Int. Cl.
*D06M 10/06* (2006.01)
*C23C 14/20* (2006.01)
(Continued)

(52) U.S. Cl.
CPC ........... *D06M 10/06* (2013.01); *C23C 14/205* (2013.01); *D02G 3/44* (2013.01); *D06M 10/025* (2013.01);
(Continued)

(58) Field of Classification Search
CPC .... D06M 10/06; D06M 11/83; D06M 10/025; D06M 16/00; D06M 2101/20;
(Continued)

(56) References Cited

U.S. PATENT DOCUMENTS 3,582,448 A  *  6/1971  Kimura et al. .... A41D 31/0066
                                                428/922
4,042,737 A  *  8/1977  Forsgren ................ D02G 1/002
                                                28/247

(Continued)

FOREIGN PATENT DOCUMENTS

CN        101307765       9/2007
EP        1743659 A1  *  1/2007
(Continued)

OTHER PUBLICATIONS

Dutta et al. Chitin and Chitosan:Chemistry, properties and applications, Journal of Scientific & Industrial Research, vol. 63, Jan. 2004, pp. 20-31.*

(Continued)

*Primary Examiner* — Scott R. Walshon
(74) *Attorney, Agent, or Firm* — Nixon & Vanderhye P.C.

(57) ABSTRACT

Treated HPPE yarns include elemental metal which forms a layer that adheres to the surface of the HPPE yarn and covers at least partly the surface of the HPPE yarn. The elemental metal is deposited onto the outer surface of a HPPE yarn via sputtering, preferably plasma sputtering. Articles comprising the treated HPPE yarn, a device comprising the treated HPPE yarn or the article as well as processes for preparing the treated HPPE yarn or treated HPPE yarn structure or treated HPPE yarn configuration and use of the treated HPPE yarn or an article or a device comprising the treated HPPE yarn for automotive applications, marine applications, aerospace applications, medical applications, defense applications, sports/recreational applications, architectural (Continued)

Figure 1:
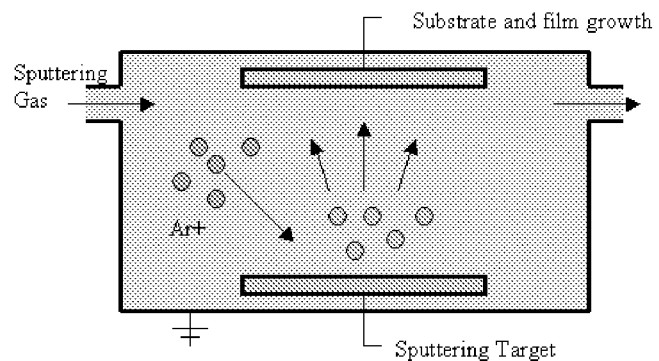

applications, clothing applications, bottling applications, machinery applications are also disclosed.

10 Claims, 3 Drawing Sheets

(51) Int. Cl.

| | |
|---|---|
| *D02G 3/44* | (2006.01) |
| *D06M 10/02* | (2006.01) |
| *D06M 11/83* | (2006.01) |
| *D06M 16/00* | (2006.01) |
| *G01N 27/20* | (2006.01) |
| *D06M 101/20* | (2006.01) |
| *G01N 33/36* | (2006.01) |

(52) U.S. Cl.
CPC ............ *D06M 11/83* (2013.01); *D06M 16/00* (2013.01); *G01N 27/20* (2013.01); *D06M 2101/20* (2013.01); *D10B 2321/0211* (2013.01); *G01N 33/36* (2013.01); *Y10T 428/2958* (2015.01)

(58) Field of Classification Search
CPC ...... D06M 11/45; D06M 11/46; D06M 11/77; D06M 11/80; D06M 11/74; D06M 2101/36; D06M 2101/06; D06M 11/05; D06M 15/03; D06M 11/00; D06M 15/01; D06M 11/47; D06M 11/49; D06M 11/44; D06M 23/16; D02G 3/44; D02G 3/02; D02G 1/002; D02G 3/449; D01D 4/02; D01D 5/18; D01F 6/04; F41J 2/00; H01Q 17/00; H01Q 15/145; H01Q 15/14; G01S 7/495; G01S 15/32; G01N 27/20; G01N 33/36; G01N 27/023; G01R 31/2648; G01R 31/2831; G01R 31/265; C23C 14/205; C23C 14/20; C23C 14/14; C08L 23/06; C08L 53/02; C08L 2203/12; A41D 31/0022; A41D 31/0077; A41D 31/00; A42B 3/06; A42B 3/10; A42B 3/04; A61L 2/232; A61L 2/16; A61L 17/04; A61L 27/16; A01N 25/34; A01N 59/16; A01N 2300/00; F41H 5/0485; F41H 1/02; F41H 5/04; F41H 5/00; F41H 1/00; F41H 5/0471; D10B 2321/0211; D10B 2231/021; B05D 3/06; B41N 1/247; D04B 19/00; A63B 71/08; B32B 15/14; D03D 15/00

USPC ............... 324/226, 236, 227, 229, 439, 693; 428/389, 194, 357, 364, 394, 336, 381, 428/433, 469, 472, 392, 395, 402, 375, 428/378, 379; 442/230, 232, 131, 379, 442/317; 604/365; 424/443; 427/501, 427/171, 222, 250, 255.24, 296, 513, 427/407.1, 252

See application file for complete search history.

(56) References Cited

U.S. PATENT DOCUMENTS

| | | | | |
|---|---|---|---|---|
| 4,302,721 | A | * 11/1981 | Urbanek et al. | .............. 324/226 |
| 5,021,258 | A | 6/1991 | McGarry | |
| 5,599,585 | A | * 2/1997 | Cohen | ..................... C23C 14/20 |
| | | | | 427/171 |
| 6,284,679 | B1 | * 9/2001 | Schilling et al. | ............. 442/230 |
| 2005/0154361 | A1 | * 7/2005 | Sabesan | ........................ 604/365 |
| 2006/0134390 | A1 | 6/2006 | Lin et al. | |
| 2007/0134305 | A1 | * 6/2007 | Zilberman | .................... 424/443 |
| 2009/0051181 | A1 | * 2/2009 | Goossens | .................. B66C 1/12 |
| | | | | 294/74 |
| 2009/0197494 | A1 | 8/2009 | Chang et al. | |

FOREIGN PATENT DOCUMENTS

| | | | | |
|---|---|---|---|---|
| EP | 2146002 | A1 * | 1/2010 | ............. A01N 25/34 |
| JP | 61-132652 | | 6/1986 | |
| JP | 62-253763 | | 11/1987 | |
| JP | 02-118173 | | 5/1990 | |
| JP | 2000314039 | A * | 11/2000 | |
| JP | 2001-040546 | | 2/2001 | |
| JP | 2001-248066 | | 9/2001 | |
| JP | 2010248663 | A * | 11/2010 | |
| WO | 2008/140578 | | 11/2008 | |

OTHER PUBLICATIONS

Dictionary of Engineering, Cathode Sputtering, www.dictionaryofengineering.com/definition/cathode-sputtering.html, copyright 2004 John Wiley & Sons, Inc., p. 1.*
International Search Report for PCT/EP2010/067334 dated Jul. 25, 2011.
Database WPI, Week 198850, Thomson Scientific, XP-002591417, retrieved Jul. 20, 2010, 1 page (Corresponds to JP 63270878).
Database WPI, Week 200566, Thomson Scientific, XP-002591418, retrieved Jul. 20, 2010, 1 page (Corresponds to WO 2005/073456).

* cited by examiner

MONOFILAMENT OR MULTIFILAMENT HPPE YARNS

This application is the U.S. national phase of International Application No. PCT/EP2010/067334 filed 12 Nov. 2010 which designated the U.S. and claims priority to EP 09175932.4 filed 13 Nov. 2009, the entire contents of each of which are hereby incorporated by reference.

The invention relates to a treated monofilament or multifilament yarn comprising a structural member of high performance polyethylene (HPPE), to a method for producing thereof and to uses of this treated monofilament or multifilament HPPE yarn.

Monofilament or multifilament HPPE yarns are known for their good mechanical properties such as high modulus and high tensile strength. However, untreated HPPE yarns exhibit intrinsically limited—if any—coatability. By limited coatability is meant that it is difficult to cover partly or—most importantly—fully its surface with a coating composition that has surface energy higher than that of high performance polyethylene. It is known that the lower the surface energy of a surface, the more difficult it becomes to coat it. Therefore, the use of these particular and very tenacious yarns in applications where additional physical, chemical and/or mechanical properties are required, is restricted by their limited coatability. So far, numerous attempts to directly adhere onto typical HPPE yarns either organic or inorganic coatings in order to impart to HPPE yarns additional physical, chemical and/or mechanical properties, failed to provide HPPE yarns that would preserve their tenacity and combine additional physical, chemical and/or mechanical properties. The reason is that conventional coating approaches applicable for other types of yarns, even if successful for coating HPPE yarns, they lead to an undesired compromise of the favorable mechanical properties of the HPPE yarns such as the significant decrease of the high strength of this type of yarns. For example, in order to increase the surface energy of an HPPE yarn, conventional and well-known methods such as corona, UV-exposure in the presence or in the absence of a solvent, plasma etching, wet etching, etc, were used to pre-treat HPPE yarns. Nevertheless, even these attempts that would allow for a coating to be applied at a subsequent step on this particular type of yarns, did also lead to a significant decrease of the favourable mechanical properties of HPPE yarns. The thus pre-treated HPPE yarns may present enhanced adhesion and coatability but at the same time their mechanical properties are inferior to those of the untreated ones. Therefore, further improvements are necessary in order to prepare HPPE yarns that would preserve their tenacity and combine additional physical, chemical and/or mechanical properties.

As a consequence, the favorable array of mechanical properties of an HPPE yarn cannot be used to its full potential in a variety of desired applications. For example in applications where high modulus and high tensile strength need to be combined with other physical, chemical and/or mechanical properties that cannot be derived from the HPPE yarn, such as electrical conductivity, antimicrobial activity, UV-resistance, radio opacity, adherence to substrates of higher surface energy than that of polyethylene, etc., it has not been possible so far to use monofilament or multifilament HPPE yarns.

EP 1 743 659 A1 discloses monofilament surgical sutures made from a composition containing ultra high molecular weight polyethylene. Plasma etching of the ultra high molecular weight polyethylene is used as a treatment of the monofilament suture to increase its surface roughness, thus increasing the adhesion of a coating to the monofilament. EP 1 743 659 A1 does not disclose compositions comprising elemental metal such as silver, titanium, etc. In addition, EP 1 743 659 A1 is silent on the effect this treatment has on the mechanical properties of the treated monofilament in respect to the mechanical properties of the untreated one.

U.S. Pat. No. 6,979,491 B2 discloses a natural or synthetic antimicrobial yarn which contains about 0.2 to 1.5% by weight of nanosilver particles (diameter between 1 and 100 nm) adhered thereto. The silver of the nanosilver particles is made by reducing silver nitrate with a reducing agent, preferably glucose, vitamin C or hydrazine hydrate ($H_2NNH_2.H_2O$). The reduction of silver nitrate takes place by mixing an aqueous solution of silver nitrate with an aqueous solution of the reducing agent. U.S. Pat. No. 6,979,491 is silent on compositions comprising high performance polyethylene let alone on providing solution on enhancing the coatability of HPPE yarns.

It would therefore be desirable to obtain a treated monofilament or multifilament HPPE yarn which would present at least comparable or suitably enhanced mechanical properties and it would offer enhanced coatability, upon comparison to the untreated monofilament or multifilament HPPE yarn. Thus, such a treated HPPE yarn would ultimately open up an array of new opportunities in numerous fields such as domestic, consumer, medical, personal protection, ballistics, fishing, recreation, etc. based on HPPE yarns' inherently favourable mechanical properties and enhanced coatability from which new physical and/or chemical properties, such as electrical conductivity, antimicrobial activity, UV-resistance, etc., would stem from.

The object of the present invention is to address some or all of the problems or disadvantages identified herein. More particularly, it is the object of the present invention to provide a treated monofilament or multifilament HPPE yarn. The improvement may for example be to provide a new monofilament or multifilament HPPE yarn which will present at least comparable mechanical properties in respect to the mechanical properties of an untreated UHMWE yarn and at the same time the new HPPE yarn to have enhanced coatability.

Therefore, broadly in accordance with the invention there is provided: A treated HPPE yarn comprising:
  an elemental metal;
  the elemental metal forms a layer that adheres to the surface of the HPPE yarn and covers at least partly the surface of the HPPE yarn, wherein the elemental metal is deposited to the outer surface of a HPPE yarn via sputtering, preferably plasma sputtering.

The treated HPPE yarns of the present invention provide for enhanced coatability of for example a coating composition coated on top of the layer formed by the elemental, and at the same time comparable mechanical properties in comparison to typical untreated HPPE yarns.

Treated monofilament or multifilament HPPE yarns of the present invention can also exhibit one or more enhanced properties such as electrical conductivity, adhesion to metallic or organic coatings, UV-resistance, radio opacity, antimicrobial activity, anti-fouling activity, aesthetics (surface appearance, surface roughness), anti-thrombogenic activity, and thermal properties.

By enhanced properties as used herein is meant that the relevant property of the treated HPPE yarn of the present invention is >+15% of the value of the known reference HPPE yarn described herein, more preferably >+17%, even more preferably >+20%, most preferably >+25%.

By comparable properties as used herein is meant that the value of the treated HPPE yarn of the present invention is within +/−15% of the value of the known reference HPPE yarn described herein, more preferably +/−12%, most preferably +/−10%.

The known reference HPPE yarn or yarn structure such as braids, for these comparisons is the commercially available HPPE yarn under the trade name Dyneema Purity® produced and marketed by DSM Dyneema B.V. or yarn structures such as braids made of this yarn.

In the context of the present invention, by "treated HPPE yarn" is meant a HPPE yarn, which HPPE yarn has been subjected to a physical and/or chemical process.

In the context of the present invention, by "treated HPPE yarn structure" is meant a HPPE yarn structure encompassing structures derived upon structuring treated HPPE yarns or structures derived upon structuring HPPE yarns which latter structures were subjected to a physical and/or chemical process.

In the context of the present invention, by "treated HPPE yarn configuration" is meant a HPPE yarn configuration encompassing configurations derived upon configuring treated HPPE yarns or configurations derived upon configuring HPPE yarns which latter configurations were subjected to a physical and/or chemical process.

In the context of the present invention, by layer is meant a thickness of some substance, such as a stratum or a coating on a surface.

In the context of the present invention the terms "monofilament or multifilament HPPE yarns", "HPPE yarns" will be used interchangeably.

In the context of the present invention the terms "method" and "process" will be used interchangeably.

In the context of the present invention the terms "HPPE yarn" and "untreated HPPE yarn" will be used interchangeably.

The percentage differences for comparable and enhanced properties herein refer to fractional differences between the treated HPPE yarn of the invention and the known reference HPPE yarn where the property is measured in the same units in the same way (i.e. if the value to be compared is also measured as a percentage, it does not denote an absolute difference).

Unless the context clearly indicates otherwise, as used herein plural forms of the terms herein (for example metal, element, yarn, monofilament, multifilament, etc.) are to be construed as including the singular form and vice versa.

For all upper and lower boundaries of any parameters given herein, the boundary value is included in each range for each parameter. All combinations of minimum and maximum values of the parameters described herein may be used to define the parameter ranges for various embodiments and preferences of the invention.

It will be understood that the total sum of any quantities expressed herein as percentages cannot (allowing for rounding errors) exceed 100%. For example the sum of all components of which the composition of the invention (or part(s) thereof) comprises may, when expressed as a weight (or other) percentage of the composition (or the same part(s) thereof), total 100% allowing for rounding errors. However where a list of components is non exhaustive the sum of the percentage for each of such components may be less than 100% to allow a certain percentage for additional amount(s) of any additional component(s) that may not be explicitly described herein.

In the context of the present invention coatability is assessed via surface tension measurements of the reference untreated HPPE yarn described herein above and of the treated HPPE yarns.

In the context of the present invention the mechanical properties assessed were elongation at break (%), E-modulus (GPa), and force-at-maximum break ($F_{max}$)(N).

For the purposes of the present invention, a yarn is herein understood to mean a product or an article the length dimension of which is much greater than its transverse diameter that can be used as an end-product or for making various other articles or devices thereof. Therefore a yarn herein includes both a yarn made of a plurality of monofilaments and a yarn made of a single monofilament.

A monofilament is herein understood to mean a filament obtainable from a single spin hole. It is noted that a monofilament herein includes a fused multifilament yarn having some monofilament characteristics, such as the one described in EP 0 740 002 A1, incorporated herein by reference. For the purposes of the present invention, a monofilament is an elongated body the length dimension of which is much greater than its transverse diameter.

In a special embodiment, the monofilaments preferably have a substantially circular or elliptical cross-section. In comparison to the yarn which is a monofilament, a multifilament yarn is herein understood as an elongated body comprising a plurality of individual monofilaments which are arranged to make up a single yarn. Multifilaments also encompass an array of monofilaments or multifilaments such as a unidirectional (UD) monolayers. Unidirectional monolayers are produced by positioning a plurality of HPPE yarns in parallel arrangement on a suitable surface and embedding the fibres in a suitable matrix material. The thus prepared network consists of a plurality of yarns unidirectionally aligned in parallel to one another along a common yarn direction.

In another special embodiment, the monofilaments can be monofilament-like, that is multifilaments at least partially melted.

When more than one filament is used, the filaments may be braided, twisted, enlarged, intertwisted or arranged in some other multifilament configuration. The yarn can be a tape or a sheet comprising one or more monofilaments or multifilaments, optionally (but not preferred) with an adhesive connecting the yarns.

In a preferred embodiment of the present invention the HPPE yarn is a monofilament.

In another preferred embodiment of the present invention the HPPE yarn is a multifilament. Multifilament encompasses also a monofilament-like structure obtained from a multifilament yarn for example as described in EP 0 740 002 A1.

In another preferred embodiment of the present invention the treated HPPE yarn is a yarn configuration or yarn structure such as for example a braid, a textile, a woven, a non-woven, a knitted, a braided or otherwise formed structure comprising the treated HPPE yarn or consisting of the treated HPPE yarn.

In a preferred embodiment of the present invention the treated monofilament or multifilament HPPE yarn comprises ultra-high molecular weight polyethylene (UHMWPE) filaments. Ultra high molecular weight polyethylene (UHMWPE) is a subset of the thermoplastic polyethylene. UHMWPE is synthesized from monomers of ethylene, which are bonded together forming molecules of polyethylene that are several orders of magnitude longer than typical high-density polyethylene (HDPE). In general, HDPE molecules have between 700 and 1,800 monomer units per molecule, whereas UHMWPE molecules tend to have 100,000 to 250,000 monomers. The molecular weight of UHMWPE is typically higher than 2 million and usually in the range between 2 to 6 million. UHMWPE is a very tough material, actually being the toughest of all known thermoplastics. UHMWPE is odorless, tasteless, and nontoxic. UHMWPE is processed using for example the following methods: compression molding, ram extrusion, gel spinning, sintering, and kneading. In gel spinning, a precisely-heated gel of UHMWPE is processed by an extruder through a spinneret. The extrudate is drawn through the air and then cooled. The end-result is a yarn with a high degree of molecular orientation, high crystallinity and therefore exceptional tensile strength. Gel spinning depends on isolating individual chain molecules in the solvent so that intermolecular entanglements are minimal. If intermolecular entanglements will not be kept to a minimum, then they are the main responsible for making a material such as UHMWPE unprocessable. In addition intermolecular entanglements can make chain orientation more difficult, lowering the mechanical strength of the final product. When UHMWPE is formed to fibers, the polymer chains can typically attain a parallel orientation greater than 90% for example greater than 95% and a high level of crystallinity for example a crystallinity of up to 85%. Polymerisation of ethylene into UHMWPE was commercialized in the 1950s by Ruhrchemie AG, which changed names over the years; today UHMWPE powder materials are produced by Ticona, Braskem, and Mitsui. UHMWPE is available commercially either as consolidated forms, such as sheets or rods, and as fibers. UHMWPE powder may also be directly molded into the final shape of a product.

In one embodiment, the HPPE also encompasses high strength polyethylene (PE) yarns for example PE yarns prepared by melt-spinning or solid state process.

In the context of the present invention, UHMWPE is herein defined as a polyethylene having an intrinsic viscosity ($\eta_{intrinsic}$) of more than 5 dl/g (deciliter per gram). Intrinsic viscosity is a measure for molecular weight that can be more easily determined from parameters such as $M_n$ and $M_w$. The $\eta_{intrinsic}$ determined according to is method PTC-179 (Hercules Inc. Rev. Apr. 29, 1982) at 135° C. in decaline, the dissolution time being 16 hours, with DBPC as the anti-oxidant in an amount of 2 g/l (gram per liter) solution, and the viscosity at different concentrations is extrapolated to zero concentration. Because of their long molecule chains, stretched polyolefin fibers with an $\eta_{intrinsic}$ of more than 5 dl/g have very good mechanical properties, such as a high tensile strength, modulus, and energy absorption at break. More preferably, a polyethylene with an $\eta_{intrinsic}$ of more than 10 dl/g is chosen. This is because such gel-spun UHMWPE yarn offers a combination of high strength, low relative density, good hydrolysis resistance, and excellent wear properties, making it particularly suited for use in various biomedical applications, including implants.

Preferably, the UHMWPE of the present invention is a linear polyethylene, i.e. a polyethylene with less than one side chain or branch per 100 carbon atoms, and preferably less than one side chain per 300 carbon atoms, a branch generally containing at least 10 carbon atoms. Preferably, only polyethylene is present, but alternatively the polyethylene may further contain up to 5 mol % of alkenes that may or may not be copolymerized with it, such as propylene, butene, pentene, 4-methylpentene or octene. The polyethylene may further contain additives that are customary for such fibres, such as anti-oxidants, thermal stabilizers, colorants, etc., up to 15% w/w of the total weight of the polyethylene plus the additives, preferably 1-10% w/w of the total weight of the polyethylene plus the additives. The UHMWPE may further be added with a polyethylene with lower molecular weight, preferably up to 10% mol of the total weight of the UHMWPE plus the polyethylene with lower molecular weight.

Monofilament or multifilament HPPE yarns have been described in various publications, including EP 0 205 960 A, EP 0213208 A1, U.S. Pat. No. 4,413,110, WO 01 73173 A1, and Advanced Fiber Spinning Technology, Ed. T. Nakajima, Woodhead Publ. Ltd (1994), ISBN 1-855-73182-7, and references cited therein, all incorporated herein by reference. In these publications, monofilament or multifilament HPPE yarns are made by a gel spinning process. Gel spun monofilament or multifilament HPPE yarns multifilament yarns have favorable mechanical properties, like a high modulus and a high tensile strength.

The diameter of a monofilament HPPE yarn is herein understood to mean the average diameter D of the HPPE yarn calculated from the dtex (g/10 km, grams of yarn per 10 Km of yarn length) of the yarn according to equation 1:

$$D(\mu m)=(4/\pi \cdot \rho^{-1} \cdot dtex \cdot 10^{-7})^{1/2} \cdot 10^6 \qquad \text{(equation 1)}$$

wherein density $\rho$ of the monofilament is assumed to be 970 kg/m$^3$.

The treated HPPE yarn according to the present invention has a diameter which is large enough to be used as a surgical suture. Filaments having a high diameter are more robust during handling (for example with regard to friction) by a surgeon and more abrasion resistant. The surgical suture sizes are defined by the United States Pharmacopeia (USP). Nowadays, the USP designations for surgical sutures range from 11-0 (the thinnest surgical sutures) to 7 (the thickest surgical sutures). Exemplary USP designations for yarns of the present invention that can be used as surgical sutures include but are not limited to, USP 11-0 (a yarn having a diameter of about 10 µm), USP 10-0 (a yarn having a diameter of about 20 µm), USP 9-0 (a yarn having a diameter of 30 µm), USP 8-0 (a yarn having a diameter of about 40 µm), USP 7-0 (a yarn having a diameter of about 50 µm), USP 6-0 (a yarn having a diameter of about 70 µm), USP 5-0 (a yarn having a diameter of about 100 µm). The higher diameter provides a higher total strength, although typically the specific strength decreases with a diameter increase. The diameter of the yarn is preferably at most 150 µm (may be used as a surgical suture of USP 4-0 designation), since it is difficult to eliminate the residual solvent to the level of 100 ppm or less. More preferably, the diameter of the yarn is at most 100 µm, even more preferably the diameter of the yarn is at most 50 µm, most preferably the diameter of the yarn is at most 40 µm, for example the diameter of the yarn is at most 30 µm. The diameter of the yarn is preferably at least 1 µm, more preferably the diameter of the yarn is at least 2 µm, even more preferably the diameter of the yarn is at least 3 µm, most preferably the diameter of the yarn is at least 5 µm, for example the diameter of the yarn is at least 6 µm.

The treated HPPE yarn according to the present invention which can be used as a surgical suture can also have a diameter higher than USP 4.0. Such sutures with diameter higher than USP 4.0 can be also obtained via a combination of yarns of smaller diameter or via yarns produced by methods such as for example compression molding, ram extrusion, gel spinning, sintering, and kneading.

In yet another embodiment of the invention, the treated HPPE yarns are tapes or films. Such tapes or films may be for example produced by feeding the HPPE to an extruder, extruding a tape or a film at a temperature above the melting point of HPPE and drawing the extruded polymeric tape or film unidirectionally or biaxially. If desired, prior to feeding the HPPE to the extruder, the HPPE may be mixed with a suitable liquid organic compound such as for example decaline or parafin, for instance to form a gel, such as is preferably the case when using UHMWPE. Another way for producing such tapes or films is via a solid state process comprising the steps of calendaring powdered HPPE at elevated temperature to form a coherent tape or film, followed by stretching the tape or film unidirectionally or biaxially. The treated HPPE tape or film can be derived by subsequently subject to a physical and/or chemical process.

In another embodiment of the invention, the treated HPPE tape or film is a porous membrane.

In an embodiment, the diameter of the treated HPPE yarn of the present invention is less than 50 μm, preferably less than 30 μm.

In another embodiment of the present invention, the treated HPPE yarn of the present invention has a diameter of about 10 to 17 μm, which can be used as a surgical suture of USP 10-0.

In yet another embodiment of the present invention, the treated HPPE yarn of the present invention, has a diameter of about 11 to 15 μm, which can be used as a surgical suture of USP 10-0.

In an additional embodiment of the present invention, the treated HPPE yarn of the present invention is large enough and can have a diameter of up to 5 mm to be used as a medical cable.

In yet another embodiment of the present invention, the treated HPPE yarn is configured to a mesh suitable for medical applications such as a medical mesh for example a hernia mesh.

In another embodiment of the present invention, an untreated HPPE yarn is configured to a mesh suitable for medical applications such as a medical mesh for example a hernia mesh and subsequently the mesh is subject to the deposition of an elemental metal that forms a layer that adheres to the outer surface of the mesh via sputtering, preferably via plasma sputtering.

The residual spin solvent is herein understood to mean the content of the solvent used in making the monofilament, which is still remaining in the final monofilament. In the process of making the yarn, any of the known solvents for gel spinning of UHMWPE can be used. Suitable examples of spinning solvents include aliphatic and alicyclic hydrocarbons, e.g. octane, nonane, decane and paraffins, including isomers thereof; petroleum fractions; mineral oil; kerosene; aromatic hydrocarbons, e.g. toluene, xylene, and naphthalene, including hydrogenated derivatives thereof, e.g. decalin and tetralin; halogenated hydrocarbons, e.g. monochlorobenzene; and cycloalkanes or cycloalkenes, e.g. careen, fluorine, camphene, menthane, dipentene, naphthalene, acenaphtalene, methylcyclopentandien, tricyclodecane, 1,2,4,5-tetramethyl-1,4-cyclohexadiene, fluorenone, naphtindane, tetramethyl-p-benzodiquinone, ethylfuorene, fluoranthene and naphthenone. Also combinations of the above-enumerated spinning solvents may be used for gel spinning of monofilament or multifilament HPPE yarns, the combination of solvents being also referred to for simplicity as spinning solvent. In one embodiment, the spinning solvent of choice has a low vapor pressure at room temperature, e.g. paraffin oil. It was also found that the process of the invention is especially advantageous for relatively volatile spinning solvents at room temperature, as for example decalin, tetralin and kerosene grades. Most preferably, the spinning solvent is decalin.

The solution of UHMWPE in a solvent is spun from a spin plate comprising one spin hole or a plurality of spin holes. Preferably, the spinning of the filament is done in a manner in which the flow rate of the solution to be spun is controlled. In one embodiment, the solution of UHMWPE is spun from a spin plate comprising a flow rate control means present before the spin hole. The flow rate control means may be a metering pump.

The control of the solution flow rate is especially advantageous in this invention, since the effect of an inconstant flow rate is larger in making a larger diameter filament. A large diameter of the spin hole gives a higher possibility that the filament has a variation in its properties over its diameter. This will result in a more homogeneous monofilament.

The combination of the large diameter and the low spin solvent residue makes the monofilament highly suitable for use in medical applications.

The residual spin solvent content of 100 ppm or less makes the cumbersome cleaning process unnecessary for use in most medical applications. Preferably, the residual solvent content is 80 ppm or less and even more preferably, 60 ppm or less. The lower solvent content makes the monofilament yarn even more suitable for some special medical applications.

The diameter of 30 μm or more allows the monofilament to be used as a yarn without further twisting or fusing process, with an advantage that there is less possibility of bacteria harboring in pores.

In one embodiment of the present invention, the treated HPPE yarn has a tenacity of 15 cN/dtex or more. Such tenacity is suitable for use in a mesh. In applications where especially high tenacity is required, such as a surgical suture, the treated HPPE yarn preferably has a tenacity of 25 cN/dtex or more.

Therefore, a treated HPPE comprising UHMWPE is provided having a diameter of 30 μm or more and a spin solvent residue of less than 100 ppm, wherein the yarn is a monofilament.

The monofilament which forms the present yarn has a diameter large enough for use as a yarn in medical applications, e.g. as a surgical suture, from handling perspective and mechanical properties. The monofilament thus does not need to be twisted to make a yarn as in multifilaments, hence reducing the required number of steps and providing a simplified method of making a yarn. Furthermore, the closed structure of the monofilament has no space for attracting bacteria.

When more than one filament is used, the filaments may be braided, twisted, enlarged, intertwisted or arranged in some other multifilament configuration. A particularly useful braid structure for surgical sutures, is the spiroid braid structure described in U.S. Pat. No. 5,019,093 and U.S. Pat. No. 5,059,213.

In one embodiment of the present invention, the treated HPPE yarn or yarn structure or yarn configuration such as a braid, a textile, a woven, a non-woven, a knitted, a braided or otherwise formed structure comprising the treated HPPE yarn or consisting of the treated HPPE, can be combined with untreated HPPE yarn or yarn structure or yarn configuration such as a braid, a textile, a woven, a non-woven, a knitted, a braided or otherwise formed structure comprising the untreated HPPE yarn or consisting of the untreated HPPE, and/or other type of yarn or yarn structure or yarn configuration such as a braid, a textile, a woven, a non-woven, a knitted, a braided or otherwise formed structure comprising the other type of yarn or consisting of the other type of yarn. Preferably, the other type of yarn or yarn structure or yarn configuration such as a braid, a textile, a woven, a non-woven, a knitted, a braided or otherwise formed structure comprising the other type of yarn or consisting of the other type of yarn, is a high-performance one such as for example, nylon yarns, teflon yarns, polypropylene yarns, etc.

By elemental metal is meant a chemical element of neutral charge having atomic number (Z) equal to 13 or atomic number Z is an integer in the range of 21 to 32 or 39 to 51 or 57 to 84. The atomic number Z (also known as the proton number) is the number of protons found in the nucleus of an atom and therefore identical to the charge number of the nucleus. The atomic number Z uniquely identifies a chemical element. In an atom of neutral charge, atomic number is equal to the number of electrons. Preferably, the elemental metal is selected from the group consisting of elemental metals with atomic number Z equal to 13 or atomic number Z is an integer in the range of 21 to 32 or atomic number Z is an integer in the range of 39 to 51, or atomic number Z is an integer in the range of 57 to 84 or mixtures thereof, more preferably the elemental metal is selected from the group consisting of elemental metals with atomic number Z equal to 13, or atomic number Z is an integer in the range of 21 to 32 or atomic number Z is an integer in the range of 39 to 51, or mixtures thereof, even more preferably the elemental metal is selected from the group consisting of elemental metals with atomic number Z equal to 13 (Al°), 22 (Ti°), 24 (Cr°), 25 (Mn°), 26 (Fe°), 28 (Ni°), 29 (Cu°), 30 (Zn°), 40 (Zr°), 46 (Pd°), 47 (Ag°), 78 (Pt°) and 79 (Au°) or mixtures thereof, most preferably the elemental metal is selected from the group consisting of elemental metals with atomic number Z equal to 13 (Al°), 22 (Ti°), 24 (Cr°), 25 (Mn°), 26 (Fe°), 28 (Ni°), 29 (Cu°), 30 (Zn°), 40 (Zr°), 47 (Ag°), 78 (Pt°) and 79 (Au°), even most preferably the elemental metal is selected from the group consisting of elemental metals with atomic number Z equal to 13 (Al°), 22 (Ti°), 24 (Cr°), 25 (Mn°), 26 (Fe°), 28 (Ni°), 29 (Cu°), 40 (Zr°), 47 (Ag°), 78 (Pt°) and 79 (Au°) or mixtures thereof, for example the elemental metal is silver (Ag°) (atomic number Z equal to 47).

In the context of the present invention, mixtures of elemental metals include also metal alloys.

The elemental metal is present in an amount of at least 0.01% w/w of the total weight of the treated HPPE yarn, preferably the elemental metal is present in an amount of at least 1.6% w/w of the of the total weight of the treated HPPE yarn, more preferably the elemental yarn is present in an amount of at least 2.1% w/w of the total weight of the treated HPPE yarn, even more preferably the elemental metal is present in an amount of at least 2.6% w/w of the total weight of the treated HPPE yarn, most preferably the elemental metal is present in an amount of at least 3.1% w/w of the total weight of the treated HPPE yarn, for example the elemental metal is present in an amount of at least 4.1% w/w of the total weight of the treated HPPE yarn. The elemental metal is present in an amount of at most 95% w/w of the total weight of the treated HPPE yarn, preferably the elemental metal is present in an amount of at least 90% w/w of the total weight of the treated HPPE yarn, more preferably the elemental yarn is present in an amount of at least 85% w/w of the total weight of the treated HPPE yarn, even more preferably the elemental metal is present in an amount of at least 80% w/w of the total weight of the treated HPPE yarn, most preferably the elemental metal is present in an amount of at least 75% w/w of the total weight of the treated HPPE yarn, for example the elemental metal is present in an amount of at least 73% w/w of the total weight of the treated HPPE yarn.

Low amounts of elemental metal, such as for example 0.01% w/w of the total weight of the treated HPPE yarn, are advantageous for treated HPPE monofilaments according to the present invention.

In a preferred embodiment, the present invention provides for the treated HPPE yarn of the present invention, wherein the elemental metal is present in an amount of at least 0.01% w/w of the total weight of the treated HPPE yarn and at most 95% w/w of the total weight of the treated HPPE yarn.

The amount of elemental metal present in the treated HPPE yarn of the present invention, can be measured via well-known chemical analysis techniques applicable for the quantitative chemical analysis of metals such as for example those described in the "Vogel's Textbook of Quantitative Chemical Analysis" ($5^{th}$ edition, John Wiley & Sons Inc., 1989) authored by G. H. Jeffery, J. Bassett, J. Mendham and R. C. Denney, or the "Quantitative Chemical Analysis" ($7^{th}$ edition, W. H. Freeman, 2006) authored by Daniel C. Harris, or other textbooks on quantitative chemical analysis available to the skilled person.

The elemental metal is deposited to a monofilament or multifilament HPPE yarn via sputtering. Sputtering is a process whereby atoms are ejected from a solid target material, typically known as the "target", due to bombardment of the target by energetic ions, typically known as "primary particles" (see FIG. 1). The ejected atoms are deposited to the surface of a substrate, typically known as the "substrate", forming a layer. It is commonly used for thin-film deposition, etching and analytical techniques such as Secondary Ion Mass Spectroscopy (SIMS). In the context of the present invention by sputtering is meant only the process used for depositing a thin layer excluding the use of sputtering for etching and/or in analytical techniques.

Atoms ejected from the target have a wide energy distribution, typically up to tens of eV (100,000 K). The ions ejected (typically only about 1% of the ejected particles is ionized) can ballistically fly from the target in straight lines and impact energetically on the substrates or vacuum chamber causing re-sputtering. At higher gas pressures, they collide with the gas atoms that act as a moderator and move diffusively, reaching the substrates or vacuum chamber wall and condensing after undergoing a random walk. The entire range from high-energy ballistic impact to low-energy thermalized motion is accessible by changing the background gas pressure. The sputtering gas is often an inert gas such as argon. For efficient momentum transfer, the atomic weight of the sputtering gas should be close to the atomic weight of the target, so for sputtering light elements neon is preferable, while for heavy elements krypton or xenon are advantageous. Reactive gases can also be used to sputter compounds. The compound can be formed on the target surface, in-flight or on the substrate depending on the process parameters. The availability of many parameters that control sputter deposition make it a complex process, but also allow experts a large degree of control over the growth and microstructure of the film.

Sputtering is driven by momentum exchange between the primary particles and atoms in the material, due to collisions. The incident ions set off collision cascades in the target. When such cascades recoil and reach the target surface with an energy above the surface binding energy, an atom can be ejected. The primary particles for the sputtering process can be supplied in a number of ways, for example by a plasma, an ion source, an accelerator or by a radioactive material emitting alpha particles.

Sputtering has a well-defined minimum energy threshold which is equal to or larger than the ion energy at which the maximum energy transfer of the primary particle to a sample atom equals the binding energy of a surface atom. This threshold typically is somewhere in the range 10-100 eV.

Different mechanisms of sputtering include but are not limited to: i) heat spike sputtering ii) preferential sputtering. Heat spike sputtering may occur when the solid is dense enough, and the incoming ion heavy enough, that the collisions occur very close to each other. Heat spike sputtering is most important for heavy ions (say Xe or Au or cluster ions) with energies in the keV-MeV range bombarding dense but soft metals with a low melting point (Ag, Au, Pb, etc.). Preferential sputtering can occur at the start when a multicomponent solid target is bombarded and there is no solid state diffusion. If the energy transfer is more efficient to one of the target components, and/or it is less strongly bound to the solid, it will sputter more efficiently than the other. If in an AB alloy the component A is sputtered preferentially, the surface of the solid will, during prolonged bombardment, become enriched in the B component thereby increasing the probability that B is sputtered such that the composition of the sputtered material will be AB.

In a preferred embodiment of the present invention, the primary particles for the sputtering process are supplied by plasma. In other words, the elemental metal is deposited to the monofilament or multifilament HPPE yarn preferably via plasma sputtering. Plasma is a partially ionized gas, in which a certain proportion of electrons are free rather than being bound to an atom or molecule. The ability of the positive and negative charges to move somewhat independently makes the plasma electrically conductive so that it responds strongly to electromagnetic fields. Plasma therefore has properties quite unlike those of solids, liquids, or gases and is considered to be a distinct state of matter. Plasma typically takes the form of neutral gas-like clouds, as seen, for example, in the case of stars. Like gas, plasma does not have a definite shape or a definite volume unless enclosed in a container; unlike gas, in the influence of a magnetic field, it may form structures such as filaments, beams and double layers. Plasma states can be divided into hot plasmas (near equilibrium plasmas) and cold plasmas (non equilibrium plasmas). Hot plasmas include electrical arcs, plasma jets of rocket engines, and thermonuclear reaction generated plasmas. They are characterized by very high temperatures of electrons and heavy particles (both charged and neutral), and they are close to 100% of ionization. Cold plasmas are composed of low-temperature particles (charged and neutral molecular and atomic species) and relatively high-temperature electrons and are associated with low degrees of ionization ($10^{-4}$ to 10%). Cold plasmas include low-pressure direct current and radio frequency (RF) discharges. The plasma commonly used for polymer surface modification can be broadly defined as a gas containing charged and neutral species, including electrons, positive and negative ions, radicals, atoms, metastables, and molecular fragments. In the plasma, the average electron temperature ranges between 1 and 10 eV, the electron density varies from $10^9$ to $10^{12}$ cm$^{-3}$, and the degree of ionization can be as low as $10^{-6}$ or as high as 0.3. An AC frequency of 50-100 kHz and above can provide a continuous discharge.

The elemental metal once deposited to the HPPE yarn forms a layer that adheres to the surface of the monofilament or multifilament HPPE yarn and covers partly or fully the surface of the monofilament or multifilament HPPE yarn. Scanning electron microscopy (SEM) on monofilament or multifilament HPPE yarns comprising elemental metal according to the present invention, can be employed to demonstrate that the elemental metal once deposited to the HPPE yarn forms a continuous layer that covers partly or fully the surface of the monofilament or multifilament HPPE yarn (see FIG. 2). By partly is meant that the surface of the HPPE yarn of the invention presents bare parts. The latter are parts of the surface of the HPPE yarn where elemental metal is not deposited to them. By fully, is meant that the surface of the HPPE yarn does not present bare parts (as defined herein above). Random and usually occurring localized layer surface defects such as pin holing, cratering, etc. may exist in either partly or fully covered surface of an HPPE yarn.

M. Amberg et al. (Plasma Process. Polym. 2008, 5, 874-880) have disclosed a plasma-assisted deposition of silver films on PET mono- and multifilament fibers. According to the present invention, it was surprisingly found that via a similar technique elemental metal for example silver, titanium, was deposited successfully to a HPPE yarn. This was surprising because it is known in the art that a PET substrate has a significantly higher surface tension than a HPPE substrate, thus PET is much easier to coat than HPPE. It is also well known in the art, the difficulty of adhering a composition, let alone elemental metal, onto a substrate of very low surface tension such as for example a HPPE substrate. The success of depositing elemental metal according to the present invention is associated to the fact that the elemental metal adhered to the surface of the HPPE yarn and covered at least partly the surface of the HPPE yarn. As far as the inventors are concerned, the present invention is the first so far, to disclose such successful deposition of elemental metal to a HPPE yarn.

Preferably, the elemental metal once deposited to the HPPE yarn forms a continuous layer that covers fully the surface of the monofilament of multifilament HPPE yarn. The thickness of the layer formed by the elemental metal once deposited to the HPPE yarn is at least 5 nm, preferably at least 10 nm, more preferably at least 20 nm, even more preferably at least 30 nm, most preferably at least 40 nm, for example at least 110 nm. The thickness of the layer formed by the elemental metal once deposited to the HPPE yarn is at most 1000 nm, preferably at most 900 nm, more preferably at most 800 nm, even more preferably at most 700 nm, most preferably at most 600 nm, for example at most 550 nm.

The layer of elemental metal deposited to the HPPE yarn should not be confused with the surface morphology of a yarn wherein elemental metal nanoparticles (see FIG. 3) such as for example silver nanoparticles, can be deposited via wet methods. The surface morphology and surface area of the layer of elemental metal according to the present invention has no association to the surface morphology and surface area of silver nanoparticles deposited to a yarn. Upon comparing FIGS. 2 and 3, the difference between the two kinds of surface morphologies becomes clear. Moreover, a simple way of demonstrating the difference in surface area, is by imagining tennis balls (silver nanoparticles) that are squeezed down to a few billionths of a meter. The particles are rounded because they try to minimize the surface energy as much as possible; any edges will make things more energetic since typically nature follows the path of least resistance the particles tend to spheres with as few edges as possible. The nanoparticles have a large surface area compared with the total volume. This high surface area to volume ratio is one of the most important properties about nanoparticles. There are a few basic points about making nanoparticles: a) a nucleation point is needed, a place for the metal (for example the metal can be silver as in the case of U.S. Pat. No. 6,979,491 B2) to start bonding to one another and start growing into a larger particle. For this one often needs some ingredient that can break down a metal salt such as for example silver nitrate, which is accomplished by using a reducing agent such as sodium borohydride, vitamin C, glucose, hydrazine hydrate, etc. The reducing agent reduces the silver nitrate into silver ions that are free then to bond with each other and b) need some mechanism to keep the particles at the nanoscale and stop them from ripping and growing into something much larger, is also needed. Typically, the latter is accomplished using a capping agent such as for example mercaptosuccinic acid. In the case of sputtering, the layer of elemental mental e.g. silver, formed has significantly lower surface area compared to the total volume upon compared to the surface area of elemental metal e.g. silver nanoparticles being present on a surface of equal dimensions.

Preferably, at least 50% of the total surface of a treated HPPE yarn according to the present invention is covered by the layer of elemental metal, more preferably at least 60% of the total surface of a treated HPPE yarn is covered by the layer of elemental metal, even more preferably at least 75% of the total surface of a treated HPPE yarn is covered by the layer of elemental metal, most preferably at least 85% of the total surface of a treated HPPE yarn is covered by the layer of elemental metal, for example at least 95% of the total surface of a treated HPPE yarn according to the present invention is covered by the layer of elemental metal.

In a preferred embodiment at least 99% of the total surface of a treated HPPE yarn according to the present invention is covered by the layer of elemental metal.

In a preferred embodiment the layer formed by the elemental metal once deposited onto a HPPE yarn, thus resulting to the treated HPPE yarn of the present invention, is continuous. By continuous is meant that the layer formed from the deposition of the elemental metal according to the invention is not interrupted by bare parts of the surface of the treated HPPE yarn along the periphery of the treated HPPE yarn.

The treated HPPE yarns of the present invention present another advantage over HPPE yarns having only elemental metal nanoparticles, in that the elemental metal nanoparticles of the latter yarns suffer from limited—if any—resistance to friction or abrasion due to their limited—if any—adhesion to a HPPE yarn surface, thus rendering pointless any initial efforts to deposit them onto a HPPE yarn. The limited—if any—resistance of elemental metal nanoparticles on HPPE yarn in respect to a treated HPPE yarn of the present invention can be demonstrated by comparative testing via well-known tests such as for example the peel-off adhesion test carried out with a 3M Scotch tape. Once this test is carried out on both a treated yarn of the present invention and a HPPE yarn having only elemental metal nanoparticles, the elemental metal nanoparticles will be completely or to a great extend be removed from the surface of the HPPE yarn, in contrast to the film formed by the elemental metal present in the case of the treated HPPE yarn of the present invention that will stay completely or almost in tact. As a consequence any technical effect that may be the result of the presence of elemental metal nanoparticles on a HPPE yarn, is rendered obsolete since the elemental metal nanoparticles will either not survive further process steps where external mechanical forces are applied such as friction between HPPE yarns, contact with hands or process-related pieces of machinery, or packaging, etc. Therefore, the treated HPPE yarns of the present invention can present enhanced properties such as robustness, electrical conductivity, adhesion to metallic or organic coatings, UV-resistance, radio opacity, antimicrobial activity, anti-fouling activity, aesthetics (surface appearance, surface roughness), anti-thrombogenic activity, thermal properties, over typical HPPE yarns having only elemental metal nanoparticles. In addition, the aforementioned properties of the treated HPPE yarns of the present invention will not be subject to degradation due to poor handling or demanding special care for handling, thus rendering the treated HPPE yarns of the present invention more robust over HPPE yarns having only elemental metal nanoparticles.

In another aspect of the present invention the present invention provides for a process for making a treated HPPE yarn, the process comprising the steps of:

depositing a layer of elemental metal to a HPPE yarn via sputtering using the HPPE yarn as a substrate and elemental metal or metal alloy as target material; a treated HPPE yarn is thus prepared;

optionally using the thus prepared treated HPPE yarn to prepare a yarn structure or yarn configuration such as a braid, a textile, a woven, a non-woven, a knitted, a braided or otherwise formed structure comprising the treated HPPE yarn or consisting of the treated HPPE yarn.

In a preferred embodiment, the invention provides for the treated HPPE yarn obtainable by the process as described herein above.

In another embodiment, the present invention provides for the process as described herein for making a treated HPPE yarn structure or treated HPPE yarn configuration, wherein the HPPE yarn is converted into a yarn structure or yarn configuration such as a braid, a textile, a woven, a non-woven, a knitted, a braided or otherwise formed structure comprising the HPPE yarn prior to the step of depositing the layer of elemental metal to the yarn structure or to the yarn configuration.

In another embodiment, the present invention provides for the process as described herein for making a treated HPPE yarn structure or treated HPPE yarn configuration, wherein the HPPE yarn is converted into a yarn structure or yarn configuration such as a braid, a textile, a woven, a non-woven, a knitted, a braided or otherwise formed structure consisting of the HPPE yarn prior to the step of depositing the layer of elemental metal to the yarn structure or to the yarn configuration.

In a preferred embodiment, the invention provides for the treated HPPE yarn, treated HPPE yarn structure or treated HPPE yarn configuration such as a braid, a textile, a woven, a non-woven, a knitted, a braided or otherwise formed structure comprising the HPPE yarn or consisting of the HPPE yarn, obtainable by the process as described herein above.

In another aspect, the present invention provides for an article comprising a treated HPPE yarn or yarn structure or yarn configuration such as a braid, a textile, a woven, a non-woven, a knitted, a braided or otherwise formed structure comprising the treated HPPE yarn or consisting of the treated HPPE yarn, of the present invention. In the context of the present invention, an article is an individual object or item or element of a class designed to serve a purpose or perform a special function and can stand alone. Exemplary articles include but are not limited to, cables, ropes, cables, ropes, cables, slings, textiles, gloves, fishing nets, surgical repair articles for example sutures (known also as surgical sutures), medical cables, medical meshes. By surgical repair article is herein understood an article for use in a medical procedure as for example a suture for repairing soft body tissue, or as a medical cable, tape, ribbon or band for repairing or retaining body parts like bones, as a (hernia) mesh or as a temporary or permanent implant. A preferred group of surgical repair articles according to the present invention are sutures, medical cables and medical meshes. Good examples of medical cables include a trauma fixation cable, a sternum closure cable, and a prophylactic or per prosthetic cable, long bone fracture fixation cable, small bone fracture fixation cable. Also tube-like products for e.g. ligament replacement are considered. A good example of a medical mesh is hernia mesh. Sutures, medical cables and medical meshes are a preferred group of surgical repair articles because these articles based on the present invention can be engineered to poses one or more optimized properties particularly desired in these articles via the enhanced coatability and at the same time comparable mechanical properties in comparison to typical surgical repair articles comprising untreated HPPE yarn or yarn structure or yarn configuration. For example, sutures according to the present invention can be used in non-invasive port-surgery tracking of the progress of a patient's tissue recovery without the suture itself intervening with for example X-ray imaging of the part of the tissue under recovery due for example the suture's radio-opaque properties.

In another embodiment, the present invention provides for the process as described herein for making an article for example a surgical repair article for example a suture, comprising an HPPE yarn prior to the step of depositing the layer of elemental metal to the yarn structure or to the yarn configuration.

In another embodiment, the present invention provides for the process as described herein for making an article for example a surgical repair article for example a suture, consisting an HPPE yarn prior to the step of depositing the layer of elemental metal to the yarn structure or to the yarn configuration.

In a preferred embodiment, the invention provides for the article for example a surgical repair article for example a suture, comprising an HPPE yarn obtainable by the process as described herein.

In another embodiment, the present invention provides for a device comprising an article of the present invention. According to the present invention, a device is a piece of equipment or a mechanism designed to serve a special purpose or perform a special function and can consist of more than one article (multi-article assembly). Exemplary devices include but are not limited to, surgical sutures together with a needle and an anchor, catheter, valves such as heart valves but also endless loop products, bag-like, balloon-like products and other woven and/or knitted products.

In a further embodiment of the present invention, any of the processes mentioned herein can be carried out in a continuous manner without interruption, typically known as a continuous process or in an interrupted manner typically known as a batch process. Preferably any of the process mentioned herein is a continuous process.

In yet another embodiment, the present invention provides for a use of the treated HPPE yarn of the invention for medical applications. Good examples of products for medical application include medical cables, medical meshes and surgical sutures. The latter preferably should have an extremely high purity since it is used for example for stitching wound, which is susceptible to infection. A surgical suture consisting of the yarn according to the present invention is especially advantageous because of its purity, less risk of attracting bacteria and/or of its anti-thrombogenic properties. Monofilaments have a stiff and smooth surface, which combine to reduce entanglement. This is also an advantage during the operation of closing wounds. Another example is a medical mesh comprising the monofilament yarn according to the present invention. The purity of the yarn and less risk of harboring bacteria is also advantageous for the surgical mesh. Moreover, the high flexibility and the light weight of the treated HPPE yarn make it especially suitable for use as a mesh.

In a preferred embodiment, the present invention provides for a use of a surgical repair article for example a suture or medical cable or medical mesh, preferably a suture for tissue repair.

Recently, one of the trends and a key-requirement for articles or devices to be used for minimal invasive surgery applications is radiopacity. Radiopacity refers to the relative inability of electromagnetism to pass through a particular material, particularly X-rays. Materials that prevent the passage of electromagnetic radiation through them are called 'radio opaque'. The term refers to the relative opaque white appearance in radiographic imaging, when passing x-rays through matter. In modern medicine, radiopaque substances are those that will not allow X-rays or similar radiation to pass. Radiologic imaging has been revolutionized by radio opaque dyes, or contrast media, which can be passed through the blood stream, the intestinal tract, or into the cerebral spinal fluid and utilized to highlight computed tomography (CT) or X-ray images. Radiopacity is one of the key considerations in the design of various devices such as guide wires or stents that are used during radiological intervention. The radiopacity of a given article or medical device such as an endovascular device is important since it allows the device to be tracked during the interventional procedure.

In another aspect, the present invention provides for the use of:
  a treated HPPE yarn of the present invention;
  an article of the present invention; or
  a device of the present invention,
for automotive applications (car parts, etc.), marine applications (ships, boats, rigging in yachting/ships, sails, slings, fishing lines, cables, etc.), aerospace applications (planes, helicopters, etc.), medical applications (joint arthroplasty, orthopedic and spine implants, for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products, etc.), defence applications (ballistic protection, body armor, ballistic vests, ballistic helmets, ballistic vehicle protection, etc.), sports/recreational applications (fencing, skates, skateboarding, snowboarding, suspension lines on sport parachutes, paragliders, kites, kite lines for kite sports, climbing equipment, bow strings, racquet strings, spear lines for spear guns, edge protection on rinks and boards, etc.), architectural applications (windows, doors, (pseudo-)walls, cables, etc.), clothing (gloves, protective clothing/equipment, textiles, etc.), bottling applications, machinery applications (can and bottle handling machine parts, moving parts on weaving machines, bearings, gears,), etc.

In yet another embodiment, the invention provides for the use of the treated HPPE yarn of the present invention for automotive applications (car parts, etc.), marine applications (ships, boats, rigging in yachting/ships, sails, slings, fishing lines, cables, etc.), aerospace applications (planes, helicopters, etc.), medical applications (joint arthroplasty, orthopedic and spine implants for example meniscus implants, surgical sutures, meshes for example hernia meshes, fabrics, woven or non-woven sheets, tapes, ribbons, bands, artificial joints, cables such as trauma fixation cables, sternum closure cables, prophylactic or per prosthetic cables, long bone fracture fixation cables, small bone fracture fixation cables, tube-like products for e.g. ligament replacement, endless loop products, bag-like, balloon-like products, etc.), defence applications (ballistic protection, body armor, ballistic vests, ballistic helmets, ballistic vehicle protection, etc.), sports/recreational applications (fencing, skates, skateboarding, snowboarding, suspension lines on sport parachutes, paragliders, kites, kite lines for kite sports, climbing equipment, bow strings, racquet strings, spear lines for spear guns, edge protection on rinks and boards, etc.), architectural applications (windows, doors, (pseudo-)walls, cables, etc.), clothing (gloves, protective clothing/equipment, textiles, etc.), bottling applications, machinery applications (can and bottle handling machine parts, moving parts on weaving machines, bearings, gears,), etc., wherein the treated HPPE yarn is used in an amount and in a format that allows the treated HPPE yarn to exhibit its electrical conductivity and/or antimicrobial properties and/or radio opacity and/or anti-thrombogenic properties and/or anti-fouling properties.

In another embodiment, the present invention provides for the use of treated HPPE yarns of the present invention for fishing lines and fishing nets with anti-fouling properties.

In a special embodiment, the present invention provides for the use of treated HPPE yarns of the present invention, wherein the elemental metal is $Ag°$ for fishing lines and/or fishing nets with anti-fouling properties. Biofouling or fouling or biological fouling is the undesirable accumulation of microorganisms, plants, algae, and/or animals on wetted surfaces or structures. The resistance and/or prevention of fouling is called anti-fouling.

Method of indication for retirement or failure detection of a treated HPPE yarn or an article or a device of the present invention, wherein:
- a treated HPPE yarn or an article or a device of the present invention, is provided;
- measure electrical conductivity or electrical resistivity between at least two longitudinally distant points on the yarn;
- compare electrical conductivity or electrical resisistivity measurements acquired at different times;
- detect failure or discard the treated HPPE yarn or article or device, if change in electrical conductivity is equal or lower than the one recommended for the treated HPPE yarn or for the article or for the device of the present invention.

For example, a rope having HPPE yarn 5% w/w of total weight of the rope with an aluminium contact according to the invention and HPPE yarn 0-95% w/w of the total weight of the rope, without an aluminium contact (the rest till 100% w/w of the total weight of the rope being balanced for example by another polymeric yarn such as nylon, PTFE, etc.,), may be discarded when the electrical DC or AC electrical conductivity has decreased by more than for example 10% over the initial electrical DC or AC electrical conductivity.

In a preferred embodiment, the invention provides for the measurement of the electrical conductivity or electrical resistivity via DC measurements.

In a most preferred embodiment the invention provides for the measurement of the electrical conductivity or electrical resistivity via AC measurements.

For example, it would be very advantageous to have a conductive monofilament or multifilament HPPE yarn or article or device comprising the treated HPPE yarn of the present invention such as for example a rope or a cable or a fishing line the wearing of which could be tracked by the decrease over time of its electrical DC or AC electrical conductivity or electrical resistivity. The reason is that the replacement of the article or device could take place at a time that would ensure good performance and/or safe use for its end-user, thus providing not only articles and/or devices with enhanced safety aspects but also optimizing cost/performance ratio for any application wherein these articles or devices form part of.

Another aspect of the invention is a treated HPPE yarn according to the Examples 2 and 3, described herein.

Many other embodiments of the invention will be apparent to those skilled in the art and such variations are contemplated within the broad scope of the present invention.

Further aspects of the invention and preferred features thereof are given in the claims herein.

An individual feature or combination of features from an embodiment of the invention described herein, as well as obvious variations thereof, are combinable with or exchangeable for features of the other embodiments described herein, unless the person skilled in the art would immediately realise that the resulting embodiment is not physically feasible.

The present invention will now be described in detail with reference to the following non limiting examples which are by way of illustration only.

FIG. 1 presents a schematic representation of sputtering [in the scheme argon (Ar) gas (sputtering gas) is used to generate the primary particles].

Figure 2:
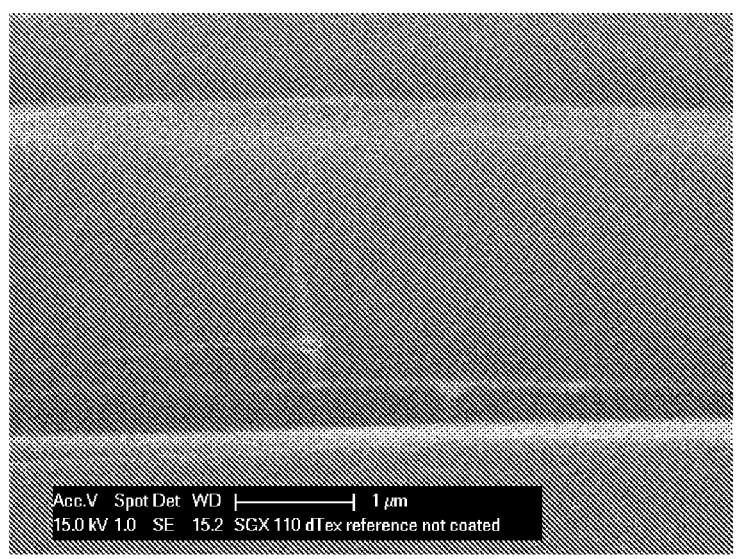

FIG. 2 presents a Scanning Electron Microscopy (SEM) image of the untreated HPPE yarn of Example 1.

Figure 3:
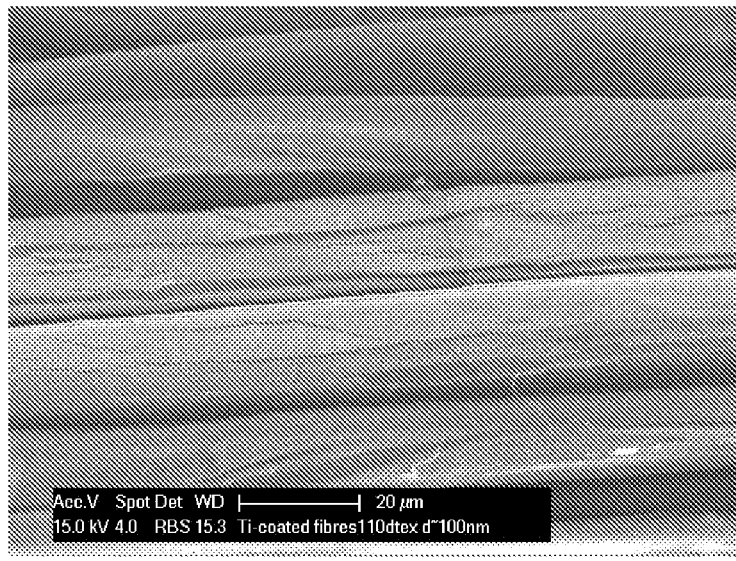

FIG. 3 presents a Scanning Electron Microscopy (SEM) image of the titanium sputtered HPPE yarn of Example 5.

Figure 4:
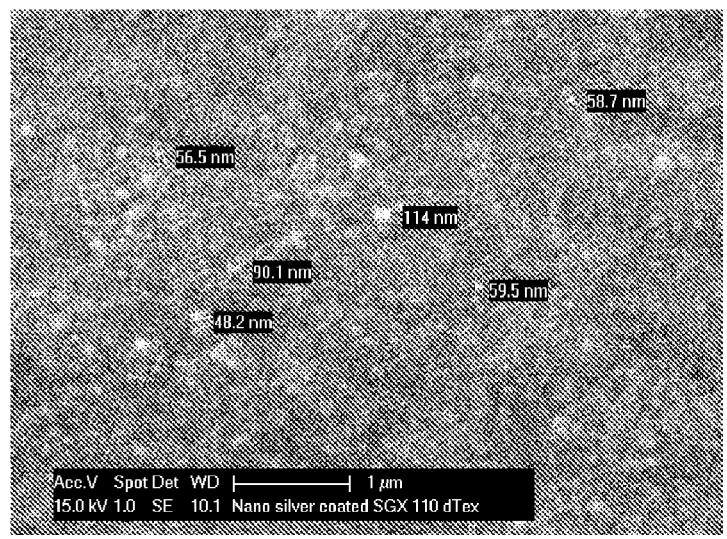

FIG. 4 presents a Scanning Electron Microscopy (SEM) image of a HPPE yarn having only silver nanoparticles.

Figure 5:
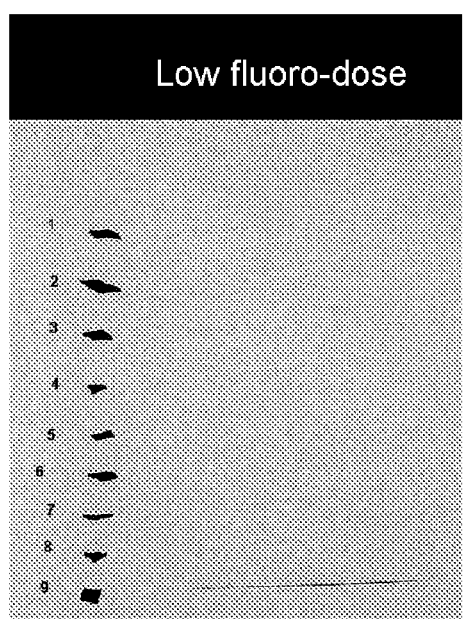

FIG. 5 presents a top-down X-ray contrast image of a sample material consisting of a polyurethane matrix (simulating a body) within which two pieces of HPPE braids, a silver sputtered and a non-silver sputtered, both simulating an implant were incorporated.

EXAMPLES

The following non limiting examples which are by way of illustration only, they refer to yarns and to a surgical repair articles for example a suture which in the Examples is referred as "braid". For example Examples 2 and 4 refer to a surgical repair article, which in Examples 2 and 4 is a suture.

Methods & Techniques for Assessing Properties Related to the HPPE Yarns and Braids The diameters of the HPPE yarns were calculated according to equation 1.

Assessment of the Electrical Conductivity of the HPPE Braids

The electrical resistance (Ohm) of an object is a measure of its opposition to the passage of a steady electric current. A digital electrical multimeter Voltcraft VC150 was used to measure the electrical DC resistance of an HPPE yarn construction. The construction was a braid of 16×1×110 dtex. The electrical contacts were placed in the two ends of the braid over a distance of 1 m in between them. Resistance's reciprocal quantity is electrical conductance measured in siemens (S). Electrical conductance is a measure of how easily electricity flows through an object.

Assessment of the Surface Tension of the HPPE Braids

The assessment of the surface tension of HPPE yarn constructions, braids of 8×1×110 dtex, was carried out according to a modified method based on ISO 8296 which measures the average wettability of PE (polyethylene) or PP (polypropylene) or PVC (polyvinylchloride) films. The modification used in the present invention is that instead of: a) using a PE film, b) depositing the test liquid (liquid of known surface tension) via a brush stroke and c) assessing the wetting of the surface after 2 seconds, the method has been modified by: a) using a surface of HPPE braid (see surface preparation below), b) dropping a droplet of the test liquid onto the HPPE braid surface and c) assessing the wetting of the surface after 3 seconds.

More particularly, the HPPE braid to be tested was wound axially and on the width dimension around a glass plate measuring 8 cm×4 cm×0.3 cm (length×width×height) in a manner such as each winding of the braid was in constant contact with the previous winding of the braid and that it resulted in complete coverage of the glass surface by a single layer of the wound HPPE braid. Once the single layer of the wound HPPE braid was secured into place, a droplet of 5 μL of a liquid of known surface tension was placed on the surface with the help of a pipette. If the droplet spread out within 3 seconds, then the surface of the braid had a surface tension equal to that of the liquid of known surface tension. The experiment was initiated using the liquid with the lower surface tension and proceeded sequentially with liquids of increasing surface tension.

The set of liquids of known surface tension was Series C (mixtures of ethanol and water) covering a surface tension range from 28 mN/m up to and including 72 mN/m, in steps of 2 mN/m. This set of liquids was supplied by TIGRES Dr. Gerstenberg GmbH (www.tigres.de).

Assessment of Mechanical Properties of the HPPE Yarns

The elongation at break (%), E-modulus (GPa), force-at-maximum break ($F_{max}$)(N) of the tested of the Reference HPPE yarn and of Ag-HPPE yarn as well as of Ti-HPPE yarn were measured as follows: a specimen of yarn was extended until breakage using a tensile testing machine, and the breaking force and the elongation at break are recorded. The sample preparation and conditioning were done as follows: before testing, the bobbins are conditioned for at least two hours at 21° C.±1° C. and relative humidity between 40 and 75%. The HPPE yarns were taken from the bobbin and placed directly into the clamps of the tensile testing machine. Any change in twist of the specimen is avoided as well as touching the part to be tested with bare hands. The actual tensile testing was carried out as follows: the tensile testing machine, Zwick 1435, was operated with a constant extension rate. The machine was equipped with Instron clamps 5681C and stainless steel clamping blocks. The clamping pressure was 6.8 bar. The extension rate was 250 mm/min and the gage length is 500 mm. A load cell with a maximum force of 1 kN was used. A pretension of 0.2 cN/dtex was applied to remove any slack from the yarn.

The maximum force-at-break ($F_{max}$)(cN, centiNewton) was the maximum force applied to rapture the sample. The elongation at break (%) was determined by 100 times the displacement of the clamps (ΔL) expressed in mm divided by the gage length ($L_o$) (500 mm). The elongation at break was not corrected for the pretension. The E-modulus (GPa) was determined by the specific stress difference (ΔF, measured in cN/dtex) between 0.3 and 1% elongation divided by the difference in elongation (0.7%) multiplied by $10^{-1}$ and subsequently multiplied the linear density of the material (measured in g/cm³) the yarn is made of. Average values for the elongation at break, E-modulus, force-at-maximum break were calculated using data from five individual tensile tests. The specific stress is determined according to the Handbook of Fibre Rope Technology, as follows:

specific stress=tension/(linear density), measured in MN/(kg/m) equal to N/tex.

Assessment of Antimicrobial Activity of the HPPE Braids

The assessment of the antimicrobial activity of the HPPE braids can be done as follows: *Escherichia coli* ATCC 11105 can be cultured from frozen stock in sterile Luria Bettani medium. The bacterial suspension has concentration of about $10^9$ CFU/mL. LB agar plates can be inoculated with 100 μL of this bacterial suspension. The HPPE yarn constructions, braids of 16×1×110 dtex can be cut into approximate 5 cm lengths; straight sections of the braids are to be used. Each braid can be pressed in the agar with sterile forceps to optimise contact with the agar surface. The agar plates can be subsequently incubated at 37° C. for 24 h in an exicator filled with a saturated salt solution to prevent dehydration of the agar. The width of the zone of growth inhibition at right angles to the braid length is to be recorded to nearest 1 mm at three spots along the braid and photographic images of the agar plates are to be generated.

Assessment of Radio Opacity of the HPPE Braids

The radio opacity of the Reference HPPE and Ag-HPPE yarn constructions, braids of 16×1×110 dtex, was assessed by X-ray irradiation on a Toshiba Infinix VC-i vascular imaging system, of a sample material consisting of a polyurethane matrix (simulating a body) within which a piece of Reference HPPE and Ag-HPPE braid (simulating an implant) were incorporated. The difference in X-ray absorption (contrast) between the polyurethane matrix which is non-radio opaque and the pieces of Reference HPPE and Ag-HPPE braids were captured by a picture (see FIG. 4).

Scanning Electron Microscopy (SEM) Analysis

SEM analysis was used to visualize the differences amongst the surface morphologies of the treated HPPE yarn of Example 5 and the untreated HPPE yarn of Example 1 as well as of the HPPE yarn of Example 6 which had only silver nanoparticles. From each of the three yarns intended for SEM analysis, a piece of yarn was used. The yarn sample of Example 2 (untreated HPPE braid) was fixed with double sided adhesive tape onto a SEM sample holder and then it was coated with a conductive Au/Pd alloy layer. The other two yarn samples were fixed with double sided adhesive tape onto a SEM sample holder without been coated with a conductive layer. Imaging was done using a Philips CPSEM XL30 at an acceleration voltage of 15 kV.

Transmission Electron Microscopy (TEM) Analysis

TEM analysis was used to measure the thickness of silver and titanium films of the treated HPPE yarns of Examples 3 and 5. The yarns of Examples 3 and 5 were placed individually and together with an epoxy resin in separate moulds. Subsequently, the epoxy resin was cured forming a hardened matrix. The hardened matrix contained the hardened epoxy resin and the braid embedded within the hardened matrix. The hardened matrix was sliced perpendicular to the braid's direction with the help of a microtome into 70 nm thick slices containing part of the braids. This operation was carried out at −120° C. Imaging of the 70 nm slices on the crossection side of the braids was done using a Philips CM200 transmission electron microscope at an acceleration voltage of 120 kV.

Examples 1-5

Example 1: Dyneema Purity® SGX 110 Dtex TS100: Reference HPPE Yarn

Dyneema Purity®SGX 110 dtex TS100 is a surface untreated HPPE yarn. Dyneema Purity®SGX 110 dtex TS100 was used as a reference HPPE yarn. The $F_{max}$, tenacity, elongation at break, E-modulus of these yarns are presented in Table 1.

Example 2: Dyneema Purity® Braid: Reference HPPE Braid

Some Reference HPPE yarns of Example 1 were constructed in braids of 16×1×110 dtex with 14.9 stitches per cm. The surface tension, electrical conductivity, antimicrobial activity and radio opacity of these braids are presented in Table 1.

Example 3: Silver Sputtered Dyneema Purity®SGX 110 Dtex TS100 Yarn: Ag-HPPE Yarn Dyneema Purity®SGX 110 dtex TS100 was magnetron sputtered with silver as follows: A pretreatment of the yarn (substrate) in Ar plasma (pressure equal to 10 Pa and power input equal to 0.04 W/cm²) was performed for 25 sec. Subsequently the target material [elemental silver (Ag°)] (sputtering target) was bombarded with primary particles generated by Ar gas (sputtering gas), under a pressure was 0.8 Pa and a power input of 0.3 W/cm². The exposure time of the yarn (substrate) was 10 min.

The amount of silver was 5.25% w/w of the total weight of the yarn plus the weight of the silver.

The thickness of the silver film was 19 nm measured by Transmission Electron Microscopy.

The $F_{max}$, tenacity, elongation at break, E-modulus of these yarns are presented in Table 1.

Example 4: Silver Sputtered Dyneema Purity® Braid: Aq-HPPE-Braid

Some Ag-HPPE-yarns of Example 3 were constructed in braids of 16×1×110 dtex with 14.9 stitches per cm. The surface tension, electrical conductivity, antimicrobial activity and radio opacity of these braids are presented in Table 1.

Example 5: Titanium Sputtered Dyneema Purity®SGX 110 Dtex TS100 Yarn: Ti-HPPE-Yarn Dyneema Purity®SGX 110 dtex TS100 was magnetron sputtered with titanium as follows: A pretreatment of the yarn (substrate) in Ar plasma (pressure equal to 10 Pa and power input equal to 0.04 W/cm²) was performed for 25 sec. Subsequently the target material [elemental titanium (Ti°)] (sputtering target) was bombarded with primary particles generated by Ar gas (sputtering gas), under a pressure was 0.8 Pa and a power input of 1.0 W/cm². The exposure time of the yarn (substrate) was 20 min.

The amount of titanium was 8.6% w/w of the total weight of the yarn plus the weight of the silver.

The thickness of the titanium film was 100 nm measured by Transmission Electron Microscopy.

The $F_{max}$, tenacity, elongation at break, E-modulus are presented in Table 1.

Example 6: Preparation of HPPE Yarn Having Only Silver Nanoparticles: NanoAq-HPPE-Yarn (Comparative Sample for the SEM Analysis)

Dyneema Purity®SGX 110 dtex TS100 is a surface untreated HPPE yarn and it was used to prepare a HPPE yarn having only silver nanoparticles as follows: A Dyneema Purity®SGX 110 dtex TS100 yarn was dipped into a commercially available silver nanoparticles suspension under the name of Ag 506-Terpineol-50% (provided by Nano-Size Ltd., in Migdal Ha'Emek, Israel, www.nano-size.com) at room temperature. The liquid medium of the silver nanoparticles suspension was terpineol, the solid content of the suspension was 50% w/w and the suspension contained a dispersant of up to 3% w/w. The yarn remained in the silver nanoparticles suspension for 10 seconds. Subsequently, the yarn was removed from the silver nanoparticles suspension and excess of the suspension was squeezed out from the yarn by applying a gentle pressure equal to 1.8 bar, in between rubber rolls. The yarn was then dried by heating it in an oven at 50° C. for 30 minutes.

TABLE 1

Mechanical and other properties of Reference HPPE yarn and Reference HPPE braid, Ag-HPPE-yarn, Ag-HPPE-braid as well as Ti-HPPE-yarn.

|  | Properties | Example 1 Reference HPPE yarn | Example 2 Reference HPPE braid | Example 3 Ag-HPPE-yarn | Example 4 Ag-HPPE-braid | Example 5 Ti-HPPE-yarn |
|---|---|---|---|---|---|---|
| Mechanical | $F_{max}$ | 36N | 512N | 33N | 485N | 33N |
|  | Elongation at break | 3.50% | 3.40% | 3.50% | 3.50% | 3.50% |
|  | E-modulus | 97 GPa | not measured | 97 GPa | not measured | 97 Gpa |
| Other | Surface tension | not measured | 34-36 mN/m | not measured | 40-42 mN/m | not measured |
|  | Electrical conductivity | not measured | $10^{-7}$ S | not measured | $17 \times 10^{-3}$ S | not measured |
|  | Radio opacity | not measured | Non-Radio Opaque | not measured | Radio Opaque | not measured |

Upon comparing the mechanical properties such as $F_{max}$, elongation at break and E-modulus of the Ag- and Ti-HPPE yarns to those of the Reference HPPE yarn, it is evident that the Ag- and Ti-HPPE yarns presented surprisingly comparable mechanical properties to those of the Reference HPPE yarn (see Table 1).

Upon comparing the mechanical properties such as $F_{max}$, and elongation at break of the Ag-HPPE braid to those of the Reference HPPE braid, it is evident that the Ag-HPPE braid presented surprisingly comparable mechanical properties to those of the Reference HPPE braid (see Table 1).

Upon comparing the surface tension (which is associated to the coatability of a yarn or a braid) of the Ag- and Ti-HPPE braid to those of the Reference HPPE braid, it becomes obvious that the Ag- and Ti-HPPE braids presented substantially increased surface tension of approximately 17%, over that of the Reference HPPE braid.

Upon comparing the surface tension, electrical DC conductivity, antimicrobial activity and radio opacity of the Ag-HPPE braids to those of the Reference HPPE braid, it becomes obvious that the Ag-HPPE braid presented improved properties over those of the Reference HPPE braid.

Therefore, the treated HPPE yarns or braids of the present invention such as the Ag- and Ti-HPPE yarns presented surprisingly comparable mechanical properties to those of the Reference HPPE yarn and at the same time the Ag- and Ti-HPPE braids presented not only enhanced coatability but also an array of improved properties over the corresponding properties of the Reference HPPE braid.

FIG. 2 presents a Scanning Electron Microscopy (SEM) image of the untreated HPPE yarn of Example 1. The surface of the untreated HPPE yarn bears no signs of elemental metal forming a layer that adheres to the surface of the HPPE yarn.

FIG. 3 presents a Scanning Electron Microscopy (SEM) image of the titanium sputtered HPPE yarn of Example 5. As it can be clearly seen the surface of the treated HPPE yarn of Example 5 has a layer of the elemental metal (titanium in this case) that adheres to the surface of the HPPE yarn. In this sample, the layer of titanium was continuous.

FIG. 4 presents a Scanning Electron Microscopy (SEM) image of the HPPE yarn of Example 6 having only silver nanoparticles. The surface of this HPPE yarn bears clear signs of the presence of the silver nanoparticles as the latter are depicted as distinct almost round-like white spots on a dark background, the latter been attributed to the HPPE yarn. On each individual filament, randomly deposited silver nanoparticles with diameters varying between 48.2 and 114 nm, can be clearly seen. When this yarn upon its preparation as described in Example 6, is subjected to the peel-off adhesion test with a 3M Scotch tape, the vast majority of the silver nanoparticles are removed.

Upon comparing the SEM images of FIGS. 2, 3 and 4, the differences amongst the surface morphologies of the treated HPPE yarn of Example 5 and the untreated HPPE yarn of Example 1 as well as of the HPPE yarn of Example 6 having only silver nanoparticles, the difference amongst these yarns become evident. More particularly, the difference is that these yarns (untreated HPPE yarn, treated HPPE yarn according to the present invention and a HPPE yarn having only silver nanoparticles) are distinctively different yarns because not only their surface morphologies are different but also the adhesion of the elemental metal to a HPPE yarn is very different.

FIG. 5 presents a top-down X-ray contrast image of a sample material consisting of a polyurethane matrix (simulating a body) within which two pieces of HPPE braids, a silver sputtered and a non-silver sputtered, both simulating an implant were incorporated. In position 5, there is an untreated (non-silver sputtered) reference HPPE braid (Reference HPPE yarn, see Example 1) and in position 9 there is a treated (silver sputtered) HPPE braid according to the invention (Ag-HPPE braid, see Example 2). The exact position of the silver sputtered braid is clearly visible in FIG. 5, whereas the untreated HPPE braid is invisible.

The invention claimed is:

1. A treated high performance polyethylene (HPPE) yarn comprising an elemental metal deposited onto an outer surface of the yarn via plasma sputtering, wherein
the elemental metal forms a continuous layer that partly covers the surface of the yarn so as to present bare parts and localized layer surface defects, and wherein
the continuous layer of elemental metal has a thickness of at least 5 nm and at most 550 nm that adheres to an outer surface of the HPPE yarn and covers at least 75% of the outer surface of the HPPE yarn, and wherein
the elemental metal is present in an amount of at least 1.6% w/w and at most 95% w/w of the total weight of the treated HPPE yarn, and wherein
the treated HPPE yarn has a tenacity of 15 cN/dtex or more which is comparable to within +/−15% of the tenacity of an untreated HPPE yarn.

2. The treated HPPE yarn according to claim 1, wherein the elemental metal is selected from the group consisting of elemental metals with atomic number Z equal to 13 (Al°), 22 (Ti°), 24 (Cr°), 25 (Mn°), 26 (Fe°), 28 (Ni°), 29 (Cu°), 30 (Zn°), 40 (Zr°), 46 (Pd°), 47 (Ag°), 78 (Pt°), 79 (Au°) and mixtures thereof.

3. The treated HPPE yarn according to claim 1, wherein the elemental metal is silver (Ag°).

4. An article comprising the treated HPPE yarn as defined in claim 1.

5. A device comprising the article as defined in claim 4.

6. A device comprising the treated HPPE yarn as defined in claim 1.

7. The device according to claim 6, wherein the device is a device for an application selected from the group consisting of automotive applications, marine applications, aerospace applications, medical applications, defense applications, sports/recreational applications, architectural applications, clothing applications, bottling applications and machinery applications.

8. The device according to claim 6, wherein the treated HPPE yarn is present in an amount such that the treated HPPE yarn exhibits at least one property selected from the group consisting of electrical conductivity, antimicrobial properties, radio opacity, anti-thrombogenic properties and anti-fouling properties.

9. A process for making a treated high performance polyethylene (HPPE) yarn having a tenacity of 15 cN/dtex of more which is comparable to within +/−15% of the tenacity of an untreated HPPE yarn, the method comprising the steps of:
depositing a layer of elemental metal to a surface of a HPPE yarn via plasma sputtering using the HPPE yarn as a substrate and an elemental metal or metal alloy as target material to thereby obtain a treated HPPE yarn such that the deposited layer of elemental metal partly covers the surface of the yarn so as to present bare parts and localized layer surface defects; and
optionally converting the treated HPPE yarn into a yarn structure selected from the group consisting of a braid structure, a textile structure, a woven structure, a non-woven structure and a knitted structure.

10. A method for indicating retirement or failure detection of a treated high performance polyethylene (HPPE) yarn, the method comprising:
  (i) providing the treated HPPE yarn as defined in claim 1;
  (ii) measuring electrical conductivity or electrical resistivity between at least two longitudinally distant points on the treated HPPE yarn;
  (iii) comparing electrical conductivity or electrical resistivity measurements acquired at different times;
  (iv) detecting a failure of the treated HPPE yarn if a change in electrical conductivity is equal or lower than the electrical conductivity recommended for the treated HPPE yarn.

* * * * *